Figure 7:
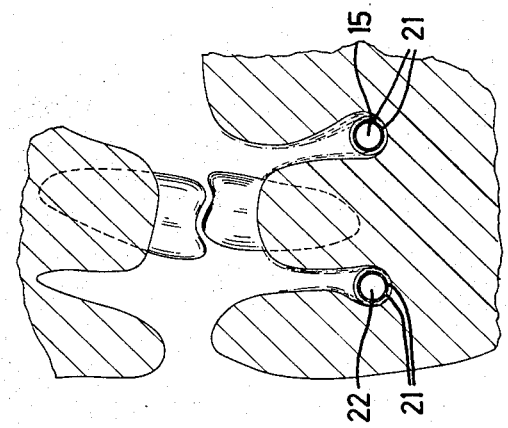

United States Patent [19]

Andersson et al.

[11] 4,417,874

[45] Nov. 29, 1983

[54] SUCTION DEVICE SUCH AS A DENTAL ASPIRATOR OR SUCKER

[76] Inventors: Bror A. E. Andersson, Enebyberg; Arne B. Mo, Stockholm, both of Sweden

[21] Appl. No.: 380,867

[22] PCT Filed: Sep. 3, 1981

[86] PCT No.: PCT/SE81/00248

§ 371 Date: May 4, 1982

§ 102(e) Date: May 4, 1982

[87] PCT Pub. No.: WO82/00764

PCT Pub. Date: Mar. 18, 1982

[30] Foreign Application Priority Data

Sep. 4, 1980 [SE] Sweden ............................ 8006160
Jun. 5, 1981 [SE] Sweden ............................ 8103566

[51] Int. Cl.³ .................................................. A61C 17/04
[52] U.S. Cl. ........................................................ 433/96
[58] Field of Search .................. 604/48, 57, 52, 51, 604/75, 76, 131, 149, 150–155, 181; 433/91, 96

[56] References Cited

U.S. PATENT DOCUMENTS 3,409,224 11/1968 Harp et al. .

FOREIGN PATENT DOCUMENTS 2240026 7/1975 France .

Primary Examiner—Robert Peshock
Attorney, Agent, or Firm—Young & Thompson

[57] ABSTRACT

A suction device such as a dental aspirator comprises a plastic tube (10) with a plurality of suction orifices (21). In accordance with the invention, at least one portion of the tube is provided with ridges and intermediate grooves (20). A plurality of small suction orifices (21) are made at least at the bottoms of the grooves, these orifices lying protected against clogging by the mucous membrane in the patient's oral cavity. The ridges and grooves comprise bellows-like folds with sides (16, 17) of different extension, so that the narrower sides (16) can be snapped in under the wide sides (17) when compressing the bellows-like portion.

2 Claims, 10 Drawing Figures

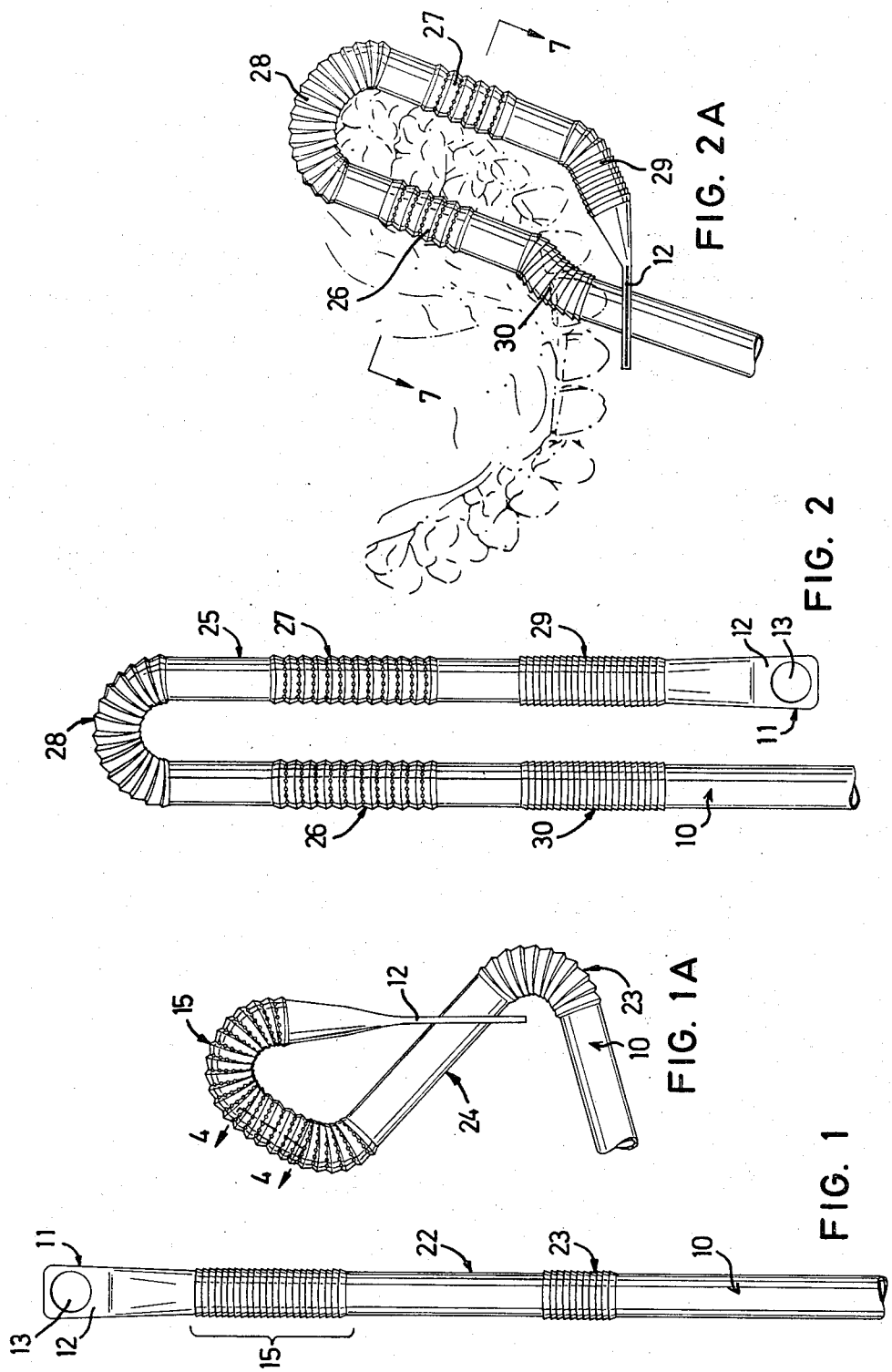

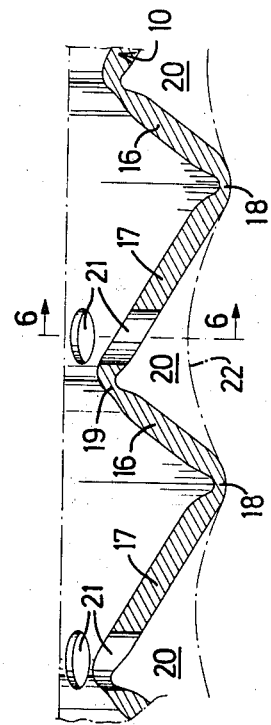
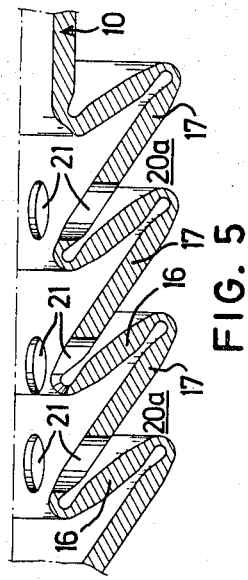
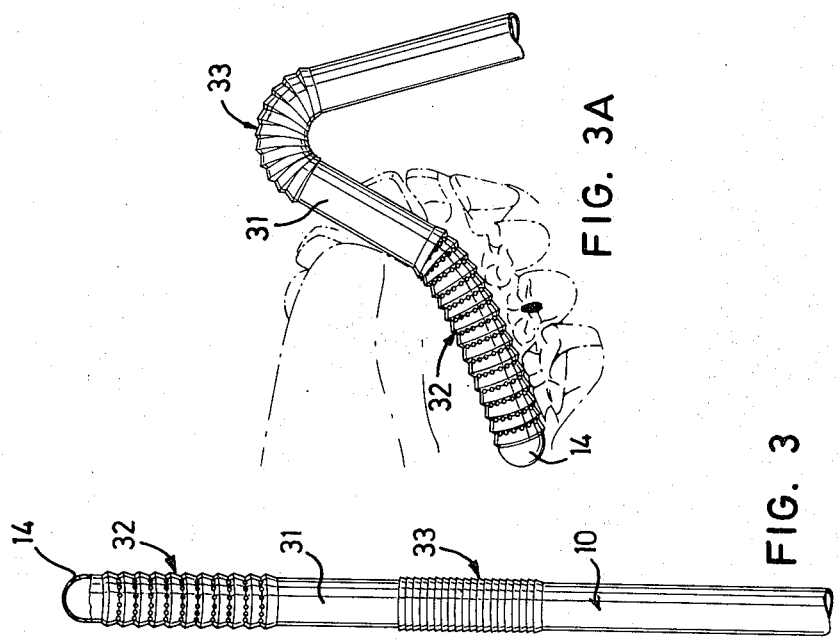

SUCTION DEVICE SUCH AS A DENTAL ASPIRATOR OR SUCKER

The present invention relates to suction devices of the kind disclosed in the preamble to the following main claim and which are used as dental aspirators or saliva suckers, the latter being used in surgical operations.

The invention primarily relates to an improved dental aspirator.

With dental aspirators it is a desire to dry out the area in question as effectively as possible, which signifies that the suction orifices of the aspirator must be as close as possible to the mucous membrane without being clogged by it.

At the present time, two main types of dental aspirators are used in practice, both comprising a plastic tube with an interiorly situated metal wire making it possible to bend the tube to a desired shape. In one type, a part of the tube is bent into a spiral running out into a bent portion, which in turn merges into a wishbone-shaped portion. The bent portion is intended to be pressed down with its underside against the mucous membrane, there being a plurality of suction orifices made in the upper side of the tube portion. Since the suction orifices open out at the surface of the cylindrical tube, there is great risk that they can be clogged by the mucous membrane, if the dental aspirator is not placed in the right way in the oral cavity. It is thus necessary now and again to check that the aspirator has not altered its position so that the suction orifices have become closed off. Another drawback with the known dental aspirator is that its end at the termination of the spiral is open, and this results in sucking-in a quite substantial quantity of leakage air, which reduces the suction ability of the aspirator at the suction orifices. Furthermore, the known dental aspirator is relatively expensive, and with regard to the fact that it is only used once, the cost per year for dental aspirators of this type for a dental practice is rather high.

A further drawback with the known dental aspirator is that it offers relatively severe resistance to bending, which can be troublesome when it is to be formed to suit the current area in the oral cavity. Since its shape is maintained with the aid of the bent metal wire, the aspirator will not adjust by itself to the oral cavity, since the bending resistance is too great for such adjustment, which results in that the aspirator can sometimes feel uncomfortable for the patient if it does not fit sufficiently well and therefore presses against certain spots in the oral cavity.

The other type of the most usual dental aspirators also comprises a flexible plastic tube with an interiorly situated metal wire. In this case there are no suction orifices in the tube. The end of the tube is instead provided with a suction head which has slit-shaped suction orifices. Since the slits are relatively long in the axial direction, it is sometimes necessary to press the suction head downwards relatively heavily against the mucous membrane so that as much as possible of the suction orifices will be placed under the saliva level in the oral cavity. In some cases, this downward pressure can be painful for the patient. This aspirator also has the drawback that the slits open out at the suction head surface and can easily be clogged by the ambient mucous membrane.

The object of the present invention is therefore to provide a dental aspirator the suction orifices of which are disposed such that they are practically completely prevented from being clogged by the mucous membrane.

This is achieved with a dental aspirator which, in accordance with the invention, has the characterizing features defined in the following claims.

The dental aspirator in accordance with the invention comprises a plastic tube which, at least at one portion along its length, is provided with a plurality of mutually separated ridges or similar protuberances, preferably extending around the circumference of the tube while forming grooves or depressions between the ridges. At least one such portion of the tube is provided with a plurality of suction orifices therein, at least at the bottoms of the grooves, and distributed along the length of the grooves. The size or diameter of the orifices is preferably less than half the depth of the groove, in such a case, so that the suction orifices at the bottoms of the grooves are well-protected against clogging by the mucous membrane.

In a preferred embodiment of the invention, the plastic tube is provided with corrugated portions formed with bellows-like folds to obtain the ridges, the suction orifices being made at least at the bottoms of the grooves between the folds. The folds are suitably made with sides of different extension, so that the short sides can snap in under the long sides when pressing together the bellows-like portion in a manner known per se, e.g. according to the U.S. Pat. No. 3,409,224. With such folding, the respective folded and compressed portions may be bent into different shapes without any great resistance, the bent portion afterwards remaining in the selected form. This brings with it great possibilities of providing different types of dental aspirators in accordance with the invention by providing the plastic tube with a plurality of such folded portions. One or some portions thus serve only to enable changing the shape of the aspirator, and are therefore not provided with suction orifices, while other portions form suction sections and are therefore provided with said suction orifices. Another advantage with this folding is that when the folds are pressed together in a certain area, the distance between the sides of the bellows-like folds will be relatively small, i.e. the width of the grooves has been decreased. The suction orifices are especially well-protected at the bottom of such a cramped groove, which signifies that particles obtained in dental treatment and other operations, for example, cannot force their way through the narrow spaces between the folds and up to the suction orifices. The folds therefore function as a kind of filter in certain areas of the folded portions.

In all the embodiments, the inner end of the tube is preferably closed off, while its outer end is connected to a source of suction. The whole suction effect thus goes to the suction orifices.

When in use, the grooves between the folds will form annular channels lying free from the mucous membranes lying on either side of the tube and under its bottom side. Saliva can thus run down along the mucous membrane on both sides of the folded portion of the dental aspirator, subsequently running down into the annular channels, where the suction orifices in the bottom of the grooves suck up the saliva.

Practical tests with the preferred embodiment having the above-mentioned bellows-like folds have shown that it is possible to dry out an area in the oral cavity in a way which is not possible with dental aspirators hitherto known.

The dental aspirator in accordance with the invention is practically completely safe with regard to avoiding clogging of the suction orifices. With the bellows-like folds, the aspirator can be very easily bent to the desired shape, and it also adjusts itself to the appropriate spaces in the oral cavity without any appreciable resistance. It is comfortable for the patient since it practically does not give rise to any pressure or stresses in the oral cavity. Furthermore, it can be manufactured to a considerably lower price than the known dental aspirators mentioned above. A still further advantage is that the aspirator in accordance with the invention takes up small storage space, since it can be delivered as a straight tube which is bent to the desired shape before use.

These and other distinguishing details and advantages of the invention will now be explained in detail in the following description of some suitable embodiments of the dental aspirator in accordance with the invention.

Figure 6:
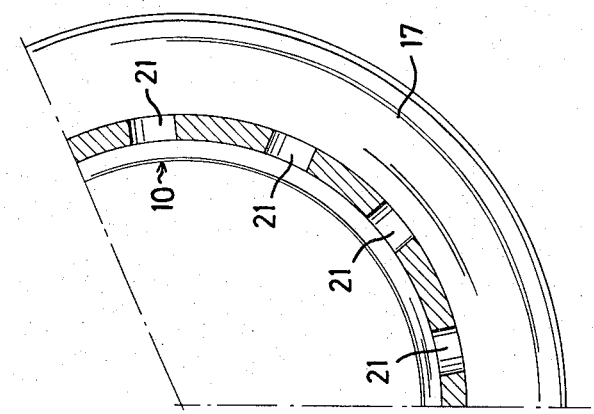

FIG. 1 is a schematic view of an embodiment of the aspirator in accordance with the invention, FIG. 1A illustrates the aspirator in a position of use, FIG. 2 schematically illustrates a second embodiment of the aspirator for sucking off saliva in the area on the inside and outside of a row of teeth according to FIG. 2A, FIG. 3 illustrates a modification of the aspirator in FIG. 1, FIG. 3A shows the aspirator of FIG. 3 in a position of use, FIG. 4 is a partial section along the line 4—4 in FIG. 1A and illustrates on an enlarged scale how the suction orifices lie protected in the extended position of the bellows-like folds at the bottoms of the grooves, FIG. 5 is the same partial section as in FIG. 4 but with the folds pressed together so that the suction orifices are even more protected, FIG. 6 is a cross section along the line 6—6 in FIG. 4 and shows a plurality of suction orifices distributed along the periphery of the grooves, and FIG. 7 is a section along the line 7—7 in FIG. 2A, showing how the two suction tube portions can receive saliva and suck dry.

The dental aspirator in the examples shown is made from plastic tube 10, e.g. polyethylene or polystyrene. The outside diameter of the tube may be within the range of 3–15 mm, depending on the field of use. In the example shown, the diameter is about 6 mm, which has been found suitable for dental aspirators.

The wall thickness of the tube may be within the range of 0.1–0.3 mm. In the example shown the wall thickness is about 0.2 mm.

The inner end 11 of the tube is closed off. In FIG. 1 the end of the tube is flattened out and welded to form a lug 12 in which there is a hole 13 for enabling the insertion of the tube 10 in the way illustrated in FIG. 1A.

In FIG. 3 the inner end of the tube is closed off with a plug or formed into a rounded-off closed end 14.

All according to the field of use of the dental aspirator, the tube can be corrugated along the major portion of its length, or it can have a plurality of corrugated portions separated by smooth cylindrical portions, the corrugations providing desired ridges and grooves situated therebetween.

In FIG. 1, a bellows-like portion is denoted by the numeral 15. As will be seen from the detail sections in FIGS. 4, 5 and 6, the bellows-like corrugations are made with alternatingly differently wide sides, i.e. narrow sides 16 and wide sides 17. At the inner edges of the sides they are joined via a hinge joint 18, and at the outer edges via a hinge joint 19. Grooves 20 are formed between the sides.

The bellows-like folds are shown in an extended position in FIG. 4, and in a compressed position in FIG. 5. On being pressed together, the narrow sides snap over a middle position to a position under the wide sides. If a compressed portion is then bent, it will remain in the bent position. The resistance to bending is relatively small in the embodiment illustrated, where the depth of the grooves is approximately half the distance between the hinge joints 18 in FIG. 4, i.e. about 1 mm.

The width of the wide sides 17 is about 1.5 times that of the narrow sides 16, and the angle between the wide and the narrow sides at the hinge joint 19 in FIG. 4 is about 90°.

With the aid of the corrugated portions in question, different types of dental aspirators can be provided from a straight tube with corrugated portions. The tube can be quickly bent with little resistance into the desired shape and fitted to the current area in the oral cavity, where the tube is further formed to the best shape by the tube adjusting itself to the existing space. The tube will thus feel comfortable to the patient simultaneously as it lies along the bottom of the cavities which are to be sucked dry.

To enable sucking away saliva, at least one of the corrugated portions is provided with a plurality of suction orifices 21, at least at the bottoms of the grooves. As will be seen from FIGS. 4 and 5, the suction orifices are located at the bottoms of the grooves and are then suitably made through the hinge joints 19 or adjacent thereto in the wide sides 17. These orifices will then be disposed so that they are protected from being clogged by the mucous membrane 22, indicated by a chain-dotted line.

The grooves 20 will be covered by the mucous membrane 22, at least along a part of their periphery. Saliva can however run down along the sides of the membrane, as will be seen from FIG. 7, and down into the groove 20 where it is sucked off through the suction orifices 21.

It is naturally not necessary for the tube only to be provided with suction orifices at the bottoms of the grooves 20. Further orifices can be provided, if so desired, in the wide and narrow sides for certain purposes, but in most cases the best suction effect is achieved without these further orifices.

As a rule, the suction orifices 21 are substantially equal in size and usually consist of small holes with a diameter which is less than half the width of the wide sides.

Instead of suction orifices 21 with a round shape, it is possible to use elongated or slit-like suction orifice openings, however.

The corrugation shown in FIG. 4 can be pressed together as is shown in FIG. 5. In this position there are obtained narrow grooves 20a which make it difficult for solid particles to reach up to the suction orifices. The groove 20a thus functions as a strainer or filter.

The illustrated embodiments of a dental aspirator in accordance with the invention meet the demands placed on a dental aspirator to a high degree, since they are considerably cheaper to manufacture than the known dental aspirators mentioned above and are easy to form to a desired shape, the tube also being able to adjust itself relatively easily to the current space in the oral cavity. Certain corrugated portions can be provided with suction orifices which lie well-protected against clogging by the mucous membrane and therefore enable effective drying-out of the operation area. The three embodiments in FIGS. 1, 2 and 3 cover the needs usually found in practice.

The dental aspirator 22 in FIG. 1 has a corrugated portion 15 with suction orifices and a corrugated portion 23 without such orifices, where the portion 15 according to FIG. 1A can be bent into a larger or smaller triangle 24. The portion 23 is bent to suspend the aspirator in the mouth. The triangle 24 forms an effective support for the patient's tongue.

In FIG. 2 there is shown a dental aspirator 25 where the tube is provided with two corrugated portions 26,27 having suction orifices, and three corrugated, flexible portions 28, 29,30 not having suction orifices and which are only intended to enable shaping the aspirator to the position of use as illustrated in FIG. 2A, where the portions 26,27 are on either side of a row of teeth for sucking up saliva.

A dental aspirator 31 is shown in FIG. 3 which has a corrugated portion 32 with suction orifices and a corrugated, flexible portion 33 without suction orifices for enabling the aspirator to hang in the mouth according to FIG. 3A.

What is claimed is:

1. In a suction tube intended as saliva sucker or surgical sucker comprising a cylindrical plastic tube (10) at least one portion of whose length is provided with a corrugation in the form of bellows folds having ridges and intermediate grooves, the bellows folds having sides (16, 17) of different widths which are so shaped and disposed that upon axial compression of the respective folded portion of the tube, the narrower sides (16) will snap over a center position to a position under the adjacent wider sides (17), whereafter any bending of the compressed portion for shaping the tube will result in the bend portion substantially remaining in its bent position; the improvement in which the bottoms of the grooves (20) have a plurality of suction openings (21) which are substantially evenly distributed along the circumference of the respective groove, one end of the tube being adapted to be connected to a suction source whereas the other end (11, 14) of the tube is closed, the suction openings being open (20a) not only when the bellows folds are in the extended position, but also when the bellows folds are in their compressed position.

2. Suction tube according to claim 1, in which the closed end (11) of the tube is compressed to a flat end portion (12) and has a hole (13) for receiving the open end of the tube to form a saliva sucker (25) in the form of a loop having at least one corrugated (26, 27) portion with suction openings (20).

* * * * *